United States Patent
Popelar et al.

(10) Patent No.: US 6,767,130 B2
(45) Date of Patent: Jul. 27, 2004

(54) SAMPLING DEVICE FOR THERMAL ANALYSIS

(75) Inventors: Patrik Popelar, Katrineholm (SE); Henrik Nyström, Katrineholm (SE)

(73) Assignee: SinterCast AB, Stockholm (SE)

( * ) Notice: Subject to any disclaimer, the term of this patent is extended or adjusted under 35 U.S.C. 154(b) by 0 days.

(21) Appl. No.: 10/307,286

(22) Filed: Dec. 2, 2002

(65) Prior Publication Data

US 2003/0086473 A1 May 8, 2003

Related U.S. Application Data

(63) Continuation of application No. 09/555,220, filed as application No. PCT/SE98/02122 on Nov. 23, 1998, now abandoned.

(30) Foreign Application Priority Data

Nov. 28, 1997 (SE) ............................................... 9704411

(51) Int. Cl.⁷ .................................................. G01K 1/12
(52) U.S. Cl. ......................................... 374/139; 374/157
(58) Field of Search ............................... 374/139, 140, 374/141, 150, 157, 179; 136/234

(56) References Cited

U.S. PATENT DOCUMENTS

| | | |
|---|---|---|
| 3,695,093 A | 10/1972 | Hummel et al. |
| 3,882,726 A | 5/1975 | Smejkal |
| 3,943,774 A | 3/1976 | Pollanz |
| 3,994,164 A | 11/1976 | Regenass et al. |
| 4,046,509 A | 9/1977 | Bäckerud |
| 4,059,996 A * | 11/1977 | Cure ............................ 374/157 |
| 4,159,307 A | 6/1979 | Shigeyasu et al. |
| 4,377,347 A | 3/1983 | Hanmyo et al. |
| 4,448,825 A * | 5/1984 | Asahara ....................... 428/34.7 |
| 4,456,389 A | 6/1984 | Regenass et al. |
| 4,515,485 A | 5/1985 | Cassidy et al. |
| 4,667,725 A | 5/1987 | Bäckerud |
| 4,804,274 A | 2/1989 | Green |
| 5,100,244 A | 3/1992 | Kniebes |
| 5,209,571 A * | 5/1993 | Kendall ....................... 374/139 |
| 5,337,799 A | 8/1994 | Bäckerud |
| 5,661,980 A | 9/1997 | Gallivan |

(List continued on next page.)

FOREIGN PATENT DOCUMENTS

| | | |
|---|---|---|
| WO | WO 96/23206 | 8/1996 |
| WO | WO 99/25888 | 5/1999 |

OTHER PUBLICATIONS

Giesserei, vol. 76, No. 9, May 1989, Eberhard Schürmann et al,"Prinzip und Probleme der thermischen Analyse einer kleinen im Sandtiegel erstarrenden legierten Metallprobe", p. 287–297, see p. 288, col. 1, line 18–line 33; fugur 7a.

Primary Examiner—Diego Gutierrez
Assistant Examiner—Yaritza Guadalupe
(74) Attorney, Agent, or Firm—Nixon & Vanderhye P.C.

(57) ABSTRACT

A sampling device for thermal analysis of solidifying metal, particularly compacted graphite iron, includes a container (2) essentially cylindrical, open at the top intended to be immersed down into and filled with a liquid metal to be analyzed, at least one temperature responsive sensor member (4), preferably two, a protective tubing (14) concentrically enclosing said sensor(s), arranged inside said container (2) and supported by a sensor support member (15) arranged above said container and attached to the container (2) by legs (16) and intended to guide and keep the sensors (4) in position, when immersed in the solidifying metal sample quantity (3) during analysis, wherein container (2) has an interior surface (17) intended to contact the sample quantity (3) during analysis, and an exterior surface (18) intended to contact the ambient atmosphere, the surfaces (17 and 18) being joined at the mouth (12) of the container (2), being equally spaced forming a closed insulating space (8), and the container (2) has a substantially semi-spherical bottom part (2b), having a concentrically arranged flattened part (2c).

16 Claims, 2 Drawing Sheets

U.S. PATENT DOCUMENTS

| | | | |
|---|---|---|---|
| 5,752,772 A | * 5/1998 | Verstreken et al. | 374/139 |
| 5,852,668 A | 12/1998 | Ishige et al. | |
| 5,932,170 A | 8/1999 | Belenkly | |
| 5,949,000 A | * 9/1999 | Lindholm et al. | 374/139 |
| 6,016,190 A | * 1/2000 | Glazman | 374/139 |
| 6,023,633 A | 2/2000 | Kado | |
| 6,050,723 A | 4/2000 | Amre | |
| 6,065,867 A | * 5/2000 | Sulmont et al. | 374/139 |
| 6,106,150 A | 8/2000 | Lindholm | |
| 6,571,856 B1 | * 6/2003 | Popelar et al. | 164/4.1 |
| 2003/0002560 A1 | * 1/2003 | Yamanaka et al. | 374/139 |

* cited by examiner

SAMPLING DEVICE FOR THERMAL ANALYSIS

CROSS REFERENCE TO RELATED APPLICATIONS

This application is a continuation of U.S. application Ser. No. 09/555,220, filed May 26, 2000, now abandoned, which is a 371 of PCT/SE98/02122, filed Nov. 23, 1998, currently pending, the specification and drawings of which are incorporated herein by reference.

BACKGROUND

The present invention relates to a sampling device for thermal analysis of solidifying metal, especially for thermal analysis in the production of castings.

Thermal analysis is a technique for monitoring variations in temperature change of molten substances during solidification to be able to determine the microstructure and hence properties of the substances in solid form. This is accomplished by taking a sample from the melt, transferring it into a sampling vessel and recording and evaluating a time-dependent temperature change in the sample during solidification, by means of temperature responsive sensor means, such as thermocouples or other devices known in the art.

When using thermal analysis for recording the solidification of molten metals, such as compacted graphite iron (CGI), it is important that the analysis is done under the same geometric and thermal conditions, as will occur in the castings. The contribution of the sampling vessel is to control the cooling during solidification of the sample of the molten metal so that the geometric and thermal conditions, in the sampling vessel are similar to those obtained in the castings. The ability to accurately measure the solidification behaviour of the molten metal allows a foundry to control its process and guarantee high quality in production.

Sampling vessels for thermal analysis are known in a large number of designs. They can be made of graphite, for use in aluminum melts, or made of a ceramic material, when intended for use with molten cast iron. However, they cannot be made of steel due to dissolution and/or thermal imbalance.

A drawback for many vessels is that they are made of materials, which are difficult to machine. Another drawback is that since they are immersed in the bulk of the metal, when taking a sample, the risk of thermal shock cracking is a problem, especially when they are made of ceramic materials, whereby they easily crack.

WO-A1-96/23206 (incorporated by reference) describes a sampling vessel to be immersed in a bath of molten metal to be analyzed. A sampling vessel is disclosed, a double-walled steel vessel with a space between the walls, having low radial thermal conductivity. The space can be filled with an insulating gas, such as air. The inner wall of the vessel is thin and thus provides a low heat capacity, so as it will easily obey a steady-state thermal condition in a short time. Furthermore, heat lost from the outer surface of the inner wall, is not let out into the ambient atmosphere, because of an outer wall, acting as a radiation shield, surrounding the inner wall and the insulating space between the walls.

The previously mentioned sampling vessel in WO-A1-96/23206 is very well suited for thermal analysis for use in CGI production on account of its special properties. However, it is expensive to manufacture, which is a disadvantage from the point of view that it can only be used once.

The thermocouples are at proper locations, i.e., one near the inner wall and one at a position, which attempts to simulate the centre of a hypothetical sphere of molten metal with uniform heat-loss per unit area. In fact the heat-loss from the bottom part is much lower, as compared to the top. One reason for this non-uniform behaviour is that the open top part emits much more heat per unit area than the rounded bottom part. Another reason is that the contact between the two surfaces at the upper joint allows heat to go around the insulting air space. This is a considerable disadvantage, since proper results are not always obtained.

It is of great importance to cool at a similar rate as the castings which are to be controlled. Equilibrium cooling would take too long to be of any practical value for this process control situation, for instance CGI production, since results would not be available before the casting process was completed, nor would it form a similar material microstructure.

Furthermore it is essential that the sampling device is not expensive, since it can only be used once. Since especially accurate measuring elements, such as thermocouples are expensive, it is preferred to reuse them several times. A major drawback with many known sampling devices is that the rather expensive thermocouples are only used once.

Yet another drawback is that it is difficult to produce large series of sampling vessels, at low cost wherein all vessels show similar properties regarding geometric and thermal conditions etc.

DISCLOSURE OF THE INVENTION

The object of the invention is to overcome these considerable disadvantages by using an improved sampling device, with a sampling container having controlled hear-loss per unit area, which simulates a sphere of molten metal, since a sphere is the most uniform, and therefore most reliable and accurate shape for thermal analysis. This sampling device having controlled heat-loss per unit area simulates a spherical solidification of the molten metal inside the sampling container, but is not spherical in shape, because of manufacturing limitations for instance. The sampling device according to the invention comprises a double-walled container, provided with a radiation shield at the top and controlled space between the walls, which has much more controlled heat-loss, does not fail at high temperatures, is not expensive and has unproved positioning of the temperature responsive sensor means, such as thermocouples, which can easily be removed and reused.

Another important problem that is solved by the invention is the shifting of a thermal centre of the simulated sphere of molten metal, which shifts downwards once the exposed top surface of the sample inside the container solidifies.

All these requirements are achieved by providing the container having the features disclosed in appended claim 1. Up till now no such sampling device has been available.

The sampling device is intended for single use, is cheap, gives reproducible geometric and thermal conditions.

It has been found that heat issuing from the exterior surface of the inner wall of the container must not immediately be let out into the ambient atmosphere, as this would make it very difficult to accomplish a controlled, slow and reproducible heat removal rate. Thus, the purpose of the outer wall is to define, together with the inner wall, a space between the walls that controls where hear is lost from the bottom and sides of the solidifying metal.

Thus, the space between the inner and the outer wall is an important parameter in regulating the heat loss due to radiation and thermal conduction. When this space is evacuated, or filled with a transparent material, such as air, radiation will be an important heat transfer mechanism. As temperature of the solidifying metal in the sampling device increases, radiation will be of increasing importance, since it's effect increases with the fourth power of absolute temperature.

By selecting and fully or partly filling the space with a suitable medium, and/or by altering the thickness of the space, it is possible to adapt the geometry of the heat removal rate of the sampling device to the values required by thermal analysis. The medium may be any known and suitable medium, such as, sand, vermiculite, mica, magnesia, chlorite, various ceramics or combinations thereof, but is preferably a gas, such as air, because of cost. In one preferred embodiment, a distance (d1) between the walls in the flattened bottom part of the container is only 5–50%, preferably about 20% of a distance (d2) between the side-walls of the container, thereby increasing the heat loss due to conduction from the bottom. Because of the reduced space at the bottom of the container, heat-loss due to conduction is increased at the bottom, balancing heat-loss from the open top of the container thereby simulating heat-loss as occured by spherical solidification of a sphere of molten metal.

Another parameter of greatest importance is the shape of the container. To be able to position temperature responsive sensor means for thermal analysis, enclosed in a protective tube, at a certain distance from the inside surface of the inner wall, the container has a flattened bottom surface. Because of practical reasons during manufacturing, both walls, i.e. the inner wall and the outer wall are made with flattened bottoms. The area of the flattened bottom part of the inner wall is at least as large as the area of a protective tube comprising sensor means to allow for a constant distance to the end of said tube. In one preferred embodiment, the diameter of said flattened bottom part area is twice the diameter of the area of the protective tube, preferably larger. The protective tube, which is partly immersed in the solidifying metal in the container has tide end to the bottom surface closed. An open protective tube does not work, since sensor means will be destroyed easily.

Furthermore, the open top part (mouth) of the container is of most importance. Heat-loss will normally be large, if not covered by a lid. Thus, the support member (See FIG. 1, item 15), comprising a radiation shield, which positions the thermocouples and is attached by legs to the container, acts as a lid to reduce radiation heat-loss from the top of the metal sample. Otherwise, the top part of the sampling device would act as a cold body, absorbing too much radiation from the hot container. This simulates heat-loss from a sphere of molten metal under solidification, as it balances slower heat-loss from the bottom of the container.

The amount of heat liberated by the initial formation of flake graphite in the near-wall region is very small, and indeed insufficient to be relied upon as a control parameter. However, if the shape of the bottom sample of the container is predominantly spherical; and, if the sampling device is preheated (for example by immersion into molten iron) thus avoiding formation of a chill zone of solidified iron in the near-wall region: and, if the sampling device is allowed to hang freely, so that heat is not extracted into a floor or mounting stand, a favourable convection current will develop within the molten iron contained in the sampling device. These convection currents "rinse" the flake graphite away from the pre-heated upper walls of the container in the sampling device and effectively concentrate the flake growth in a flow-separated region at the base of the essentially spherical container.

The inner wall of the container is preferably made rather thin and/or of a material with a low specific thermal capacity, in order to impart a desirable low total thermal capacity to the inner wall. In addition to this the inner wall has preferably a high total heat transfer coefficient, to equalize the temperature of the sample quantity and the wall; and as the total heat transfer coefficient is high, the time required to transfer the amount of heat will be short.

The inner wall can be made of any material that has the thermal properties stated as above, being thermally stable in the molten metal being sampled. Typically a metal or alloy is used. Materials that are inexpensive and ensure reliable series production, especially steel, are preferred.

It also possible to alter the colour and/or the surface finish to modify the radiation characteristics of the walls.

The interior surface of the inner wall of the container is preferably coated with a protective barrier in order to protect said wall from dissolving into or react with the hot liquid metal sample. Such protective coating could also be applied to the exterior surface of the outer wall, particularly if the container is intended to be immersed in hot liquid metal when sampling. The protective coating does not affect the thermal balance, since it is very thin. However, the coating is critical in defining the solidification behaviour. The coating can be inert or doped with reactive substances to consume Mg and induce flake graphite formation near the bottom temperature responsive sensor means. This is disclosed in Swedish patent application 9704208-9 (incorporated by reference) and for further information Swedish patent application 9003289-7 (incorporated by reference). The protective coating could be any refractory oxide such as alumina, magnesia, zirconia, silica carbide, etc.

The temperature responsive sensor means are mounted in a support member, guiding and crimping the sensor means in place. The sensors for thermal analysis are generally thermocouples, although the present invention is not limited in that sense; any kind of sensor suited for thermal analysis of solidifying metal can be used. C. f. Swedish parent application 9600720-8 infrared pyrometry (incorporated by reference).

The sensor means for thermal analysis, in the following thermocouples, are enclosed in a concentrically arranged protective tube, which is partly immersed in the solidifying metal in the container. The protective tube having one closed end is positioned and held by the support member and a thereto arranged radiation shield, i.e. firmly at two points. One thermocouple (gauge part) is inserted to the closed end of said tube, in a way that it can easily be removed. It is also critical to locate a second thermocouple measurement point (gauge part) within the thermal centre to avoid that the cooling curves shift during the measurement period. Therefore, a second thermocouple (gauge part), also removable, is inserted into the protective tube, at the thermal centre of the molten sample, preferably at a distance, c, about ⅔ of the total height a, of the inner container. Because the thermocouples are removable, they can be reused for a number of measurements. The tube enclosing the two thermocouples, is positioned as close as possible to the flattened inside bottom surface in the container, but must not contact this surface. It is essential to assure that the protective tube is completely surrounded by solidifying metal where no voids or bubbles could interfere with the measurement. Furthermore, it is of great importance that the thermosensors are firmly mounted, so that they do not move sideways, dug analysis. Inaccurate positioning of the thermocouples, is a considerable disadvantage, which interferes heavily with the measurement results. This is avoided as the thermocouples are accurately positioned by the support member and thereto arranged radiation shield, crimping the protective tube, comprising the sensors, accurately in position. The distance of the closed protective tube to die flattened bottom, b, is 1–10% of the total height of the inner container, a, preferably about 5%.

The protective tube can be made of materials, such as steel, preferably stainless steel or quartz glass. Steel tubes normally require coating. The invention is not limited to the use of only one protective tube or one pair of thermocouples. As many as necessary can be used at different distances, i.e. measurement points.

BRIEF DESCRIPTION OF THE FIGURES

The invention will now be described in snore detail with reference to the accompanying drawings in which

FIG. 1 shows sampling device 1 according to the invention, comprising a double-walled sampling container 2, which is essentially cylindrical, open at the top, having a semi-spherical bottom part 2b, provided with a flattened part 2c, filled with a sample quantity 3 of molten metal under solidification to the mouth 12 of the container, temperature responsive sensor means 4a–b for thermal analysis and a sensor support member 15, comprising a radiation shield 19 and attached by legs 16 to the container 2, said support member 15 and radiation shield 19, guiding a protective tube 14, enclosing said sensor means 4a–b, firmly in position. The gauge parts 5a–b of the temperature responsive sensor means 4a–b, in the following thermocouples, are immersed in the sample quantity 3.

Figure 1:
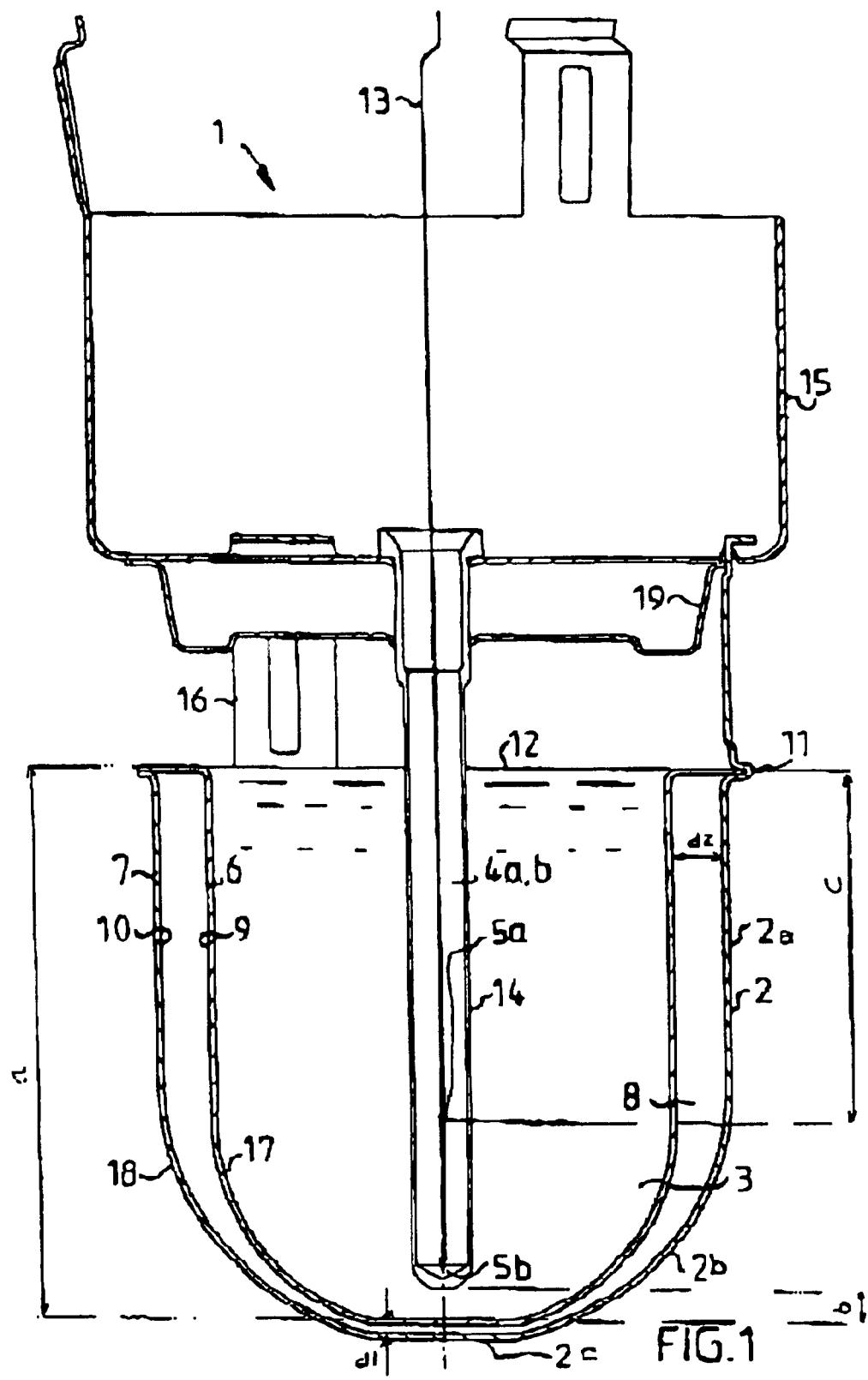
FIG. 1 is a schematic cross section through a sampling device according to an embodiment of the invention, designed for use in connection to CGI production.
Figure 2:
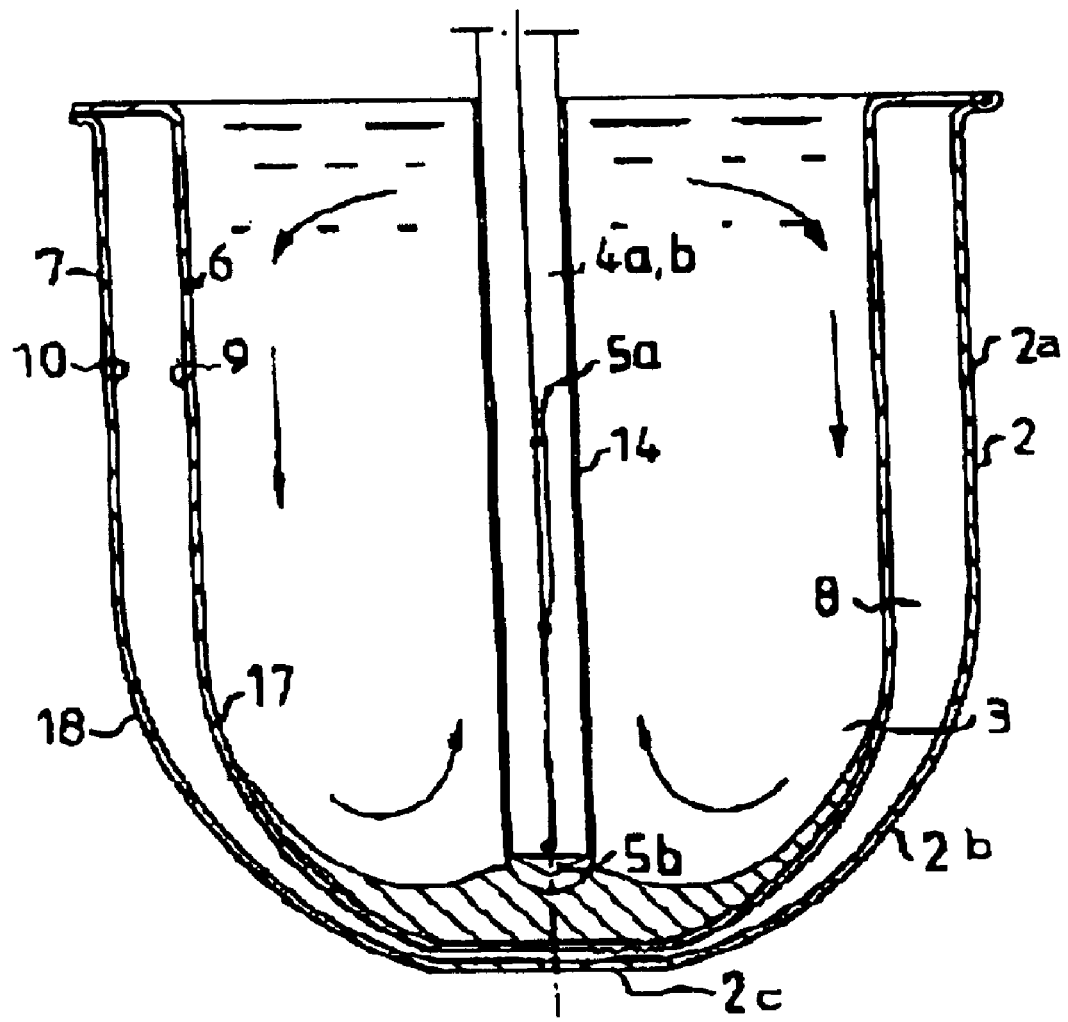
FIG. 2 demonstrates currents in a sample of solidifying molten metal and how these currents affect the layer of flake graphite cast iron normally formed in the vicinity of the container wall.

The container includes an inner wall 6 and an outer wall 7, both made of thin steel sheet metal, and in between these walls a space 8, defined by an exterior surface 9 of the inner wall 6, and the interior surface 10 of the outer wall 7. A fold 11 joins the walls 6 and 7 at the mouth 12 of the container 2. The fold 11 can also be a continuous seam or a spot weld. The space 8 is filled with air. The two thermocouples 4a–b are arranged vertically in line, inside the protective tube 14 made of steel, ceramics, glass or any other suitable material with the first thermocouple 4 (gauge part 5b) placed at a location close to an interior surface 17 of the inner wall 6, and the other thermocouple 4 (gauge part 5a) in the thermal centre, a, of the sample quantity 3. The sensor support member 15 is provided to removably hold the protective tube 14 enclosing thermocouples 4 in firm position during analysis. The thermocouples 4 are connected to a thermal analysis evaluation equipment (not shown) by a cable 13, through which measurement signals from the gauge parts 5a–b are transmitted to said equipment analysis.

The end of the protective tube 14 is located at a distance be from the flattened bottom 2c of the container 2.

During analysis liquid molten metal flows down into the container 2, between the legs 16, when immersed in the molten metal to be analyzed.

As illustrated in FIG. 1, the container 2 is always filled with molten metal having the same amount during analysis. Every sample should have the same amount of molten metal to ensure consistent thermal conditions and consistent reaction with the reactive coating. Consistent sample volume is a problem with conventional thermal analysis vessels which require pour-in filling. The present invention, with immersion-type filling and a large space for metal entry minimizes operator error and improves case-of-sampling.

The invention is not limited to the illustrative embodiments shown and instead is applicable to other embodiments. It will be understood that it lies within the expertise of a person skilled in the art, to make suitable modifications of the sampling devices, and that raid device is not limited for use in production of CGI or other forms of cast iron only, but may also be used in production of a variety of other metals.

The sampling device is preferably adapted for use in connection with production of CGI to the method disclosed in U.S. Pat. No. 4,667,725.

What is claimed is:

1. A sampling device for thermal analysis of solidifying metal, particularly compacted graphite iron, comprising:

a container that is essentially cylindrical, said container being open at a top and structured to be immersed down into and filled with a liquid metal to be analyzed, at least one temperature responsive sensor member, at least one protective tube concentrically enclosing said at least one temperature responsive sensor member, arranged inside said container and supported by a sensor support member arranged above said container and attached to said container by legs and structured to guide and keep said at least one temperature responsive sensor member in position, when immersed in a solidifying metal sample quantity during analysis, said container including an inner wall with an interior surface structured to contact the sample quantity during analysis and an exterior surface, and an outer wall with an interior surface and an exterior surface structured to contact ambient atmosphere, said walls being joined at the said top of said container and being mutually equally spaced in a cylindrical part of the container, so as to form a closed insulating space between opposite corresponding wall surfaces, wherein said container has a substantially semispherical bottom part which has a concentrically arranged flattened part with a diameter larger than the diameter of the protective tube, a distance between inner wall surfaces of the flattened part being less than a distance between those wall surfaces in the cylindrical part of the container.

2. A sampling device according to claim 1 that includes two temperature responsive sensor members.

3. A sampling device according to claim 2 that includes only one protective tube.

4. A sampling device according to claim 1 that includes only one protective tube.

5. A sampling device according to claim 1, wherein said distance between the insulating space defining wall surfaces in the flattened part is 10–50% of said distance between those wall surfaces in the cylindrical part of the container, in order to impose spherical cooling conditions on a non-spherical sampling device.

6. A sampling device according to claim 1, wherein the cylindrical part of the container has a height about twice as large as the height of the semi-spherical bottom part, in order to impose spherical cooling conditions on a non-spherical sampling device.

7. A sampling device according to claim 1, wherein said at least one sensor member is removably inserted in said protective tube at a distance from the flattened bottom part as small as possible without forming air-bubbles or voids or contacting the flattened part.

8. A sampling device according to claim 1, wherein the protective tube is made of steel.

9. A sampling device according to claim 8, wherein the protective tube is coated with a protective refractory agent.

10. A sampling device according to claim 1, wherein the protective tube is made of quartz glass.

11. A sampling device according to claim 1, wherein at least one of the interior surface and the exterior surface has been treated by brushing, etching, sand blasting or chemically and the protective tube is coated with a protective refractory agent.

12. A sampling device according to claim 1, wherein the interior surface of the container is coated with inert coating.

13. A sampling device according to claim 1, wherein the interior surface of the container is coated with reactive coating.

14. A sampling device according to claim 1, wherein at least one of the interior surface, the exterior surface and the protective tube have been treated by plasma spraying or sintering applied ceramics of alumina, magnesia, zirconia, silicon carbide, silicon nitride, carbon, boron nitride or silica.

15. A sampling device according to claim 1, wherein at least one of the colour and surface finish of the walls have been altered to modify the radiation characteristics thereof.

16. A sampling device according to claim 1 wherein cooling curves recorded near the vessel wall are recorded in a flow-separated area at the base of said container, by a gauge part of one sensor, in order to increase the resolution for evaluating undertreated metal following reaction with reactive wall coatings.

* * * * *